United States Patent
Shida et al.

(10) Patent No.: US 9,949,645 B2
(45) Date of Patent: Apr. 24, 2018

(54) FLUORESCENCE IMAGING APPARATUS FOR IDENTIFYING FLUORESCENCE REGION BASED ON SPECIFIED PROCESSING CONDITION AND SUPERIMPOSING FLUORESCENCE REGION AT CORRESPONDING REGION IN RETURN-LIGHT IMAGE

(71) Applicant: OLYMPUS CORPORATION, Tokyo (JP)

(72) Inventors: Hiromi Shida, Tokyo (JP); Yasushige Ishihara, Tokyo (JP)

(73) Assignee: OLYMPUS CORPORATION, Tokyo (JP)

(\*) Notice: Subject to any disclaimer, the term of this patent is extended or adjusted under 35 U.S.C. 154(b) by 945 days.

(21) Appl. No.: 14/033,687

(22) Filed: Sep. 23, 2013

(65) Prior Publication Data
US 2014/0024948 A1   Jan. 23, 2014

Related U.S. Application Data

(63) Continuation of application No. PCT/JP2012/055722, filed on Mar. 6, 2012.

(30) Foreign Application Priority Data

Mar. 31, 2011   (JP) ................. 2011-080633

(51) Int. Cl.
*A61B 6/00* (2006.01)
*A61B 5/00* (2006.01)
(Continued)

(52) U.S. Cl.
CPC .......... *A61B 5/0071* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS 5,735,276 A * 4/1998 Lemelson ............. A61B 18/20
                                                                250/458.1
5,769,791 A * 6/1998 Benaron ............. A61B 5/0086
                                                                600/473
(Continued)

FOREIGN PATENT DOCUMENTS

JP       10-201700 A      8/1998
JP     2002-238844 A      8/2002
(Continued)

OTHER PUBLICATIONS

International Search Report dated Apr. 10, 2012 issued in PCT/JP2012/055722.
English Abstract only of JP 2006-191989, dated Jul. 27, 2006.

*Primary Examiner* — James Kish
(74) *Attorney, Agent, or Firm* — Scully, Scott, Murphy & Presser P.C.

(57) ABSTRACT

A fluorescence imaging apparatus including: a processor comprising hardware, configured to: specify a processing condition to be used to process a fluorescence image in accordance with treatment-details information indicating specifics of a treatment to be performed on a biological tissue; in a case where a first processing condition is specified, identify a first fluorescence region in the fluorescence image having a predetermined first fluorescence intensity based on the first processing condition; in a case where a second processing condition is specified, identify a second fluorescence region in the fluorescence image having a predetermined second fluorescence intensity based on the second processing condition; and generate a superimposed image by superimposing the first fluorescence region or the (Continued)

second fluorescence region that is identified, with a return-light image at a region in the return-light image corresponding to the first fluorescence region or the second fluorescence region, respectively, that is identified.

12 Claims, 7 Drawing Sheets

(51) Int. Cl.
    *A61B 1/00* (2006.01)
    *A61B 1/04* (2006.01)
    *G02B 23/24* (2006.01)

(52) U.S. Cl.
    CPC .......... *A61B 1/043* (2013.01); *G02B 23/2469* (2013.01); *G02B 2207/113* (2013.01)

(56) References Cited

U.S. PATENT DOCUMENTS

| | | | | |
|---|---|---|---|---|
| 2004/0206913 A1* | 10/2004 | Costa | ................... | A61B 5/0059 250/458.1 |
| 2005/0059894 A1* | 3/2005 | Zeng | ................ | A61B 1/00055 600/476 |
| 2005/0145257 A1* | 7/2005 | Barrera | ............ | G06Q 10/06316 128/898 |
| 2008/0103390 A1* | 5/2008 | Contag | .............. | G01N 21/6428 600/427 |
| 2008/0123922 A1* | 5/2008 | Gielen | ..................... | A61B 5/06 382/131 |
| 2008/0200926 A1* | 8/2008 | Verard | ..................... | A61B 5/06 606/130 |
| 2009/0202119 A1* | 8/2009 | Hefti | .................... | A61B 5/0059 382/128 |
| 2010/0049058 A1* | 2/2010 | Ishihara | ................ | A61B 1/043 600/477 |
| 2010/0331624 A1* | 12/2010 | Suzuki | ................ | A61B 1/0638 600/109 |

FOREIGN PATENT DOCUMENTS

| | | |
|---|---|---|
| JP | 2003-164414 A | 6/2003 |
| JP | 2004-024656 A | 1/2004 |
| JP | 2004-089533 A | 3/2004 |
| JP | 2007-313169 A | 12/2007 |
| JP | 2009-207793 A | 9/2009 |
| JP | 4587811 B2 | 11/2010 |

* cited by examiner

FIG. 1

2 - illumination unit
3 - image processing unit
4 - treatment tool
5 - IC tag reader
7 - monitor
41 - IC tag

FLUORESCENCE IMAGING APPARATUS FOR IDENTIFYING FLUORESCENCE REGION BASED ON SPECIFIED PROCESSING CONDITION AND SUPERIMPOSING FLUORESCENCE REGION AT CORRESPONDING REGION IN RETURN-LIGHT IMAGE

CROSS-REFERENCE TO RELATED APPLICATIONS

This is a continuation of International Application PCT/JP2012/055722, with an international filing date of Mar. 6, 2012, which is hereby incorporated by reference herein in its entirety. This application claims the benefit of Japanese Patent Application No. 2011-080633, the content of which is incorporated herein by reference.

TECHNICAL FIELD

The present invention relates to a fluorescence imaging apparatus.

BACKGROUND ART

In the related art, there is a known fluorescence endoscope apparatus that, when there is a region with high fluorescence intensity in an acquired fluorescence image, identifies this region as a diseased portion and reports the presence of the diseased portion (for example, see Patent Literature 1).

CITATION LIST

Patent Literature

PTL 1 Publication of Japanese Patent No. 4587811

SUMMARY OF INVENTION

The present invention provides a fluorescence imaging apparatus provided with an illuminating portion that radiates excitation light and illumination light onto biological tissue; a fluorescence imaging portion that acquires a fluorescence image by imaging fluorescence emitted at the biological tissue; a return-light imaging portion that acquires a return-light image by imaging return light that returns from the biological tissue; a fluorescence-region identifying portion that identifies a fluorescence region in the fluorescence image acquired by the fluorescence imaging portion by using a processing condition specified from among a plurality of processing conditions; a superimposed-image generating portion that generates a superimposed image by superimposing the fluorescence region identified by the fluorescence-region identifying portion at a corresponding position in the return-light image acquired by the return-light imaging portion; an output portion that externally outputs the superimposed image generated by the superimposed-image generating portion; a treatment-information acquisition portion that acquires treatment-details information indicating specifics of treatment to be performed on the biological tissue; and an image switching portion that specifies the processing condition to be used by the fluorescence-region identifying portion from among the plurality of processing conditions in accordance with the treatment-details information acquired by the treatment-information acquisition portion.

DESCRIPTION OF EMBODIMENT

A fluorescence imaging apparatus 100 according to an embodiment of the present invention will be described below with reference to the drawings.

Figure 1:
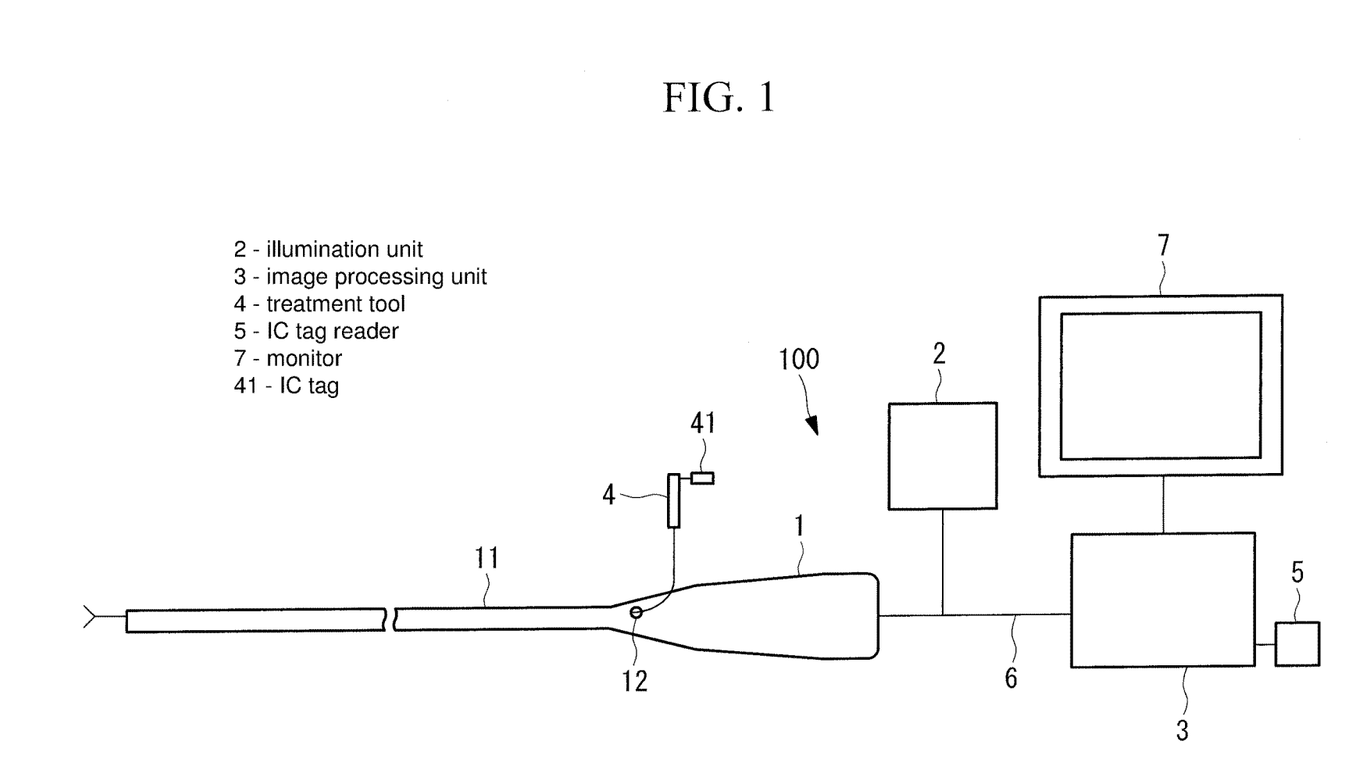
FIG. 1 is an overall configuration diagram showing a fluorescence imaging apparatus according to an embodiment of the present invention.

As shown in FIG. 1, a fluorescence imaging apparatus 100 according to this embodiment is configured based on an endoscope 1 and is used when performing endoscopic treatment of a diseased portion labeled with a fluorescent dye in a living organism. For example, by labeling biological molecules specifically existing in a diseased portion with a fluorescent dye by utilizing antibodies or the like, an operator can identify a fluorescence region in a fluorescence image acquired by the endoscope 1 as a diseased portion, and thus, he/she can treat the diseased portion.

As shown in FIG. 1, the fluorescence imaging apparatus 100 according to this embodiment is provided with an endoscope 1; an illumination unit 2 that supplies white light (illumination light) and excitation light to the endoscope 1; an image processing unit 3 that processes an image captured by the endoscope 1; and an IC tag reader 5 (treatment-information acquisition portion) that reads an IC tag 41 attached to a treatment tool 4 used in combination with the endoscope 1.

Figure 2:
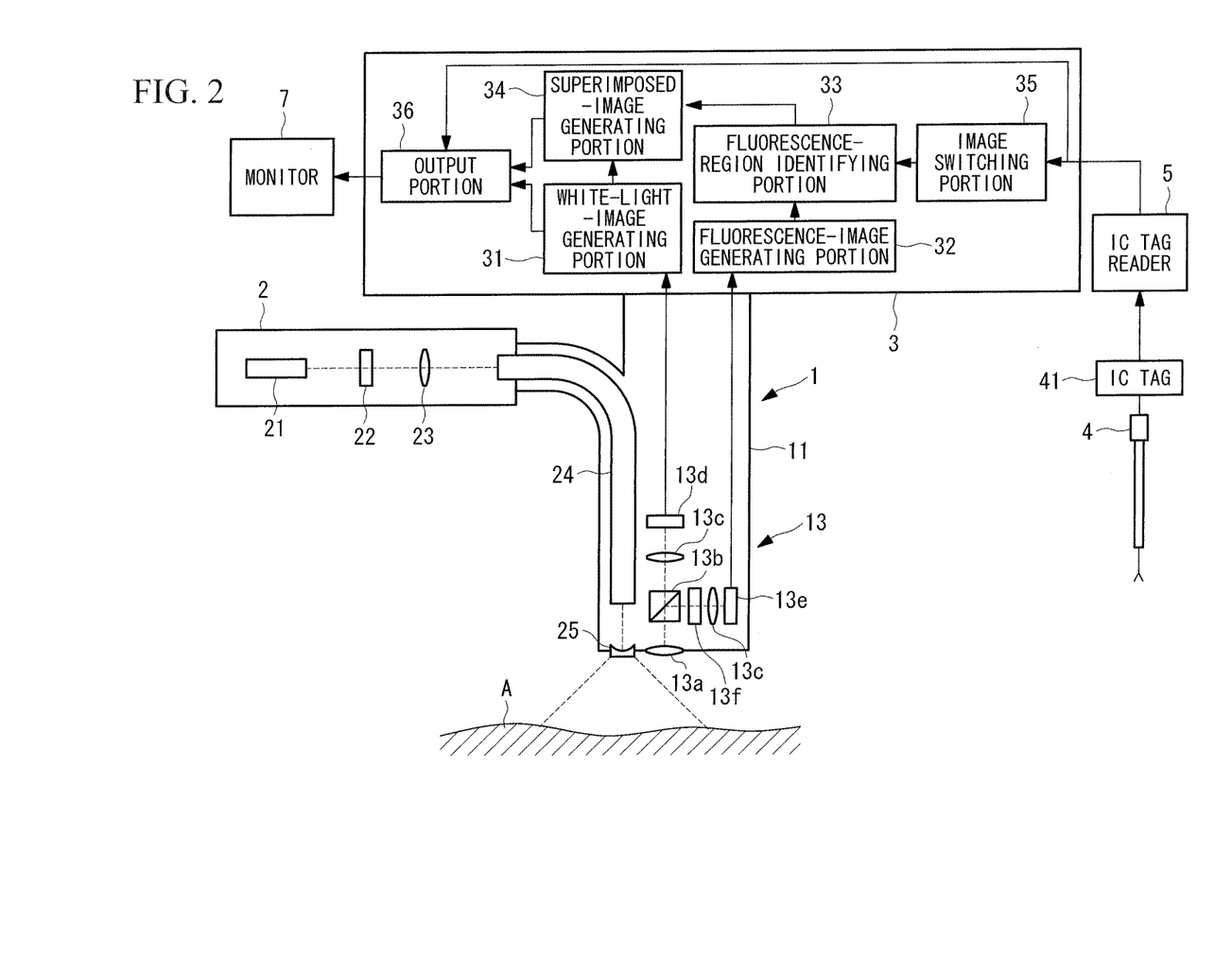
FIG. 2 is a detailed configuration diagram of the fluorescence imaging apparatus in FIG. 1.

FIG. 2 is a diagram showing the detailed configuration of the fluorescence imaging apparatus 100.

The endoscope 1 is provided with a long, thin inserted portion 11 that is inserted into a body and a channel 12 formed in the inserted portion 11 so as to pass therethrough in the longitudinal direction thereof, into which the treatment tool 4 is inserted. An imaging optical system 13 that acquires image information of biological tissue A, which is an observation subject, is provided at the distal end of the inserted portion 11.

The imaging optical system 13 is provided with an objective lens 13a that collects return light returning from a predetermined observation area in the observation subject; a dichroic mirror 13b that, of the return light collected by the objective lens 13a, reflects light having a wavelength equal to or greater than the excitation wavelength of a fluorescent dye (excitation light and fluorescence) and allows light having a wavelength shorter than the excitation wavelength to pass therethrough; two focusing lenses 13c that respectively focus the light that has passed through the dichroic mirror 13b and the light that has been reflected by the dichroic mirror 13b; and two imaging devices 13d and 13e, like CCDs, that separately capture the light focused by the focusing lenses 13c.

In the figure, reference sign 13f is an excitation-light cut filter that blocks the excitation light in the light reflected by the dichroic mirror 13b. The fluorescent dye in this embodiment is assumed to be Cy7 or the like whose excitation wavelength is a relatively long wavelength compared with that of the white light. Therefore, the light that has passed through the dichroic mirror 13b is white light, and the imaging device 13d acquires a white-light image, whereas the imaging device 13e acquires a fluorescence image. The image information acquired by the individual imaging devices 13d and 13e is transmitted to the image processing unit 3 via a cable 6.

The illumination unit 2 is provided with a light source 21 that emits light having a sufficiently wide wavelength band, such as a xenon lamp; a filter 22 that extracts the excitation light and the white light from the light emitted from the light source 21; and a coupling lens 23 that focuses the excitation light and the white light extracted by the filter 22. After guiding the excitation light and the white light focused by the coupling lens 23 through a light-guide fiber 24 disposed over nearly the entire length of the inserted portion 11 in the longitudinal direction thereof, the illumination unit 2 spreads out and radiates the light onto the observation subject by means of an illumination optical system 25 provided at the distal end of the inserted portion 11.

The image processing unit 3 is provided with a white-light-image generating portion 31 that generates a white-light image (return-light image) by using, of the image information transmitted thereto via the cable 6, white-light-image (return-light-image) information acquired by the imaging device 13d; a fluorescence-image generating portion 32 that generates a fluorescence image by using fluorescence-image information acquired by the imaging device 13e; a fluorescence-region identifying portion 33 that generates an identification image in which, based on a plurality of predetermined processing conditions, a fluorescence region is identified in the fluorescence image generated by the fluorescence-image generating portion 32; a superimposed-image generating portion 34 that generates a superimposed image in which the identification image is superimposed on the white-light image; an image switching portion 35 that determines the processing condition to be used in the fluorescence-region identifying portion 33 based on the information of IC tag 41 received by the IC tag reader 5; and an output portion 36 that outputs the image to a monitor 7.

The fluorescence-region identifying portion 33 has a first image-processing mode (first processing condition), in which substantially the entire fluorescence region where fluorescence is detected is identified, and a second image-processing mode (second processing condition), in which, from the fluorescence region where fluorescence is detected, a maximum-fluorescence region including a region where the most intense fluorescence is detected is identified in a fluorescence image. The fluorescence-region identifying portion 33 generates an identification image by using, of the first image-processing mode and the second image-processing mode, one image-processing mode specified by the image switching portion 35, described later.

Figure 3:
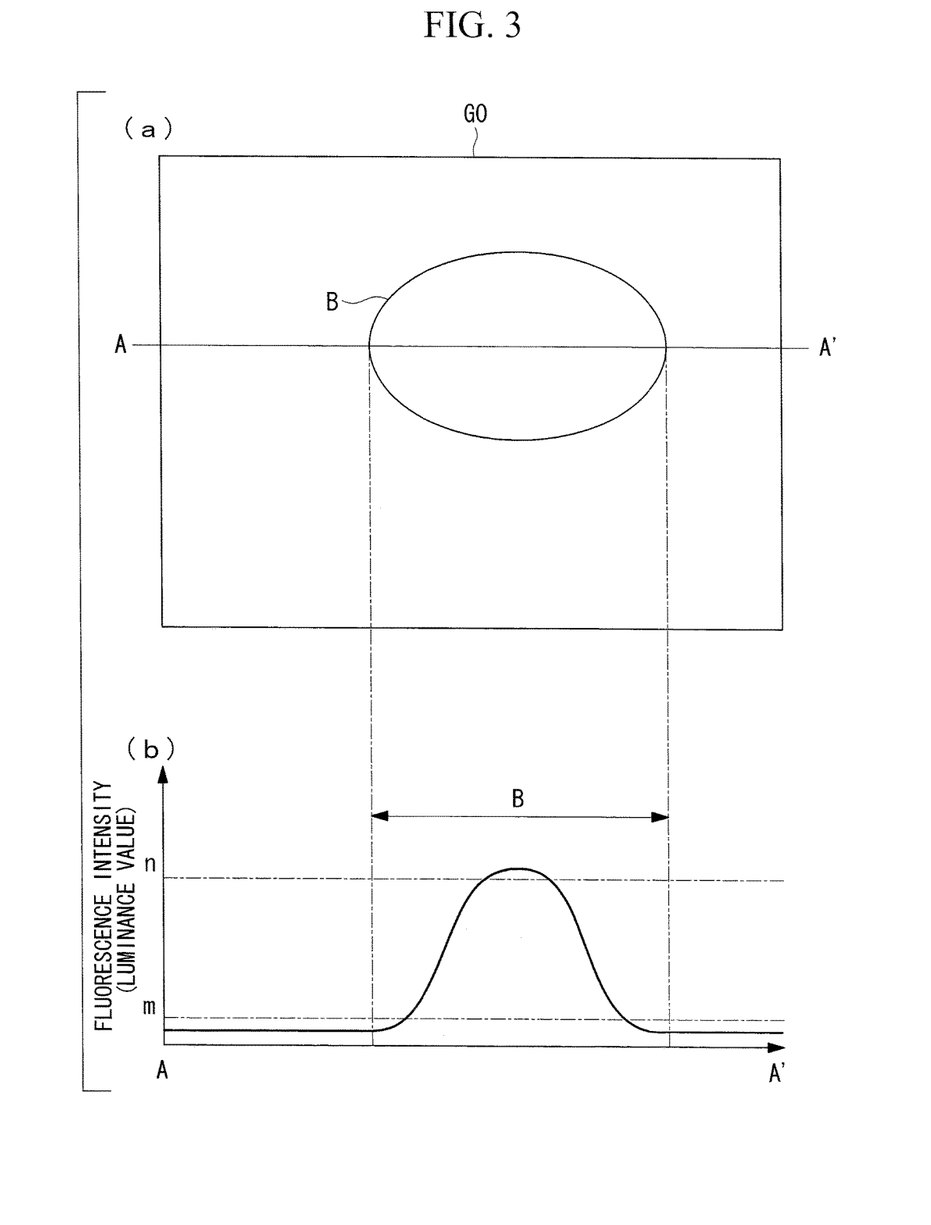
FIG. 3 is a diagram for explaining the image processing performed by a fluorescence-region identifying portion in FIG. 2, in which (a) is a fluorescence image generated by a fluorescence-image generating portion, and (b) is a graph showing the relationship between the fluorescence-intensity distribution in the fluorescence image along A-A' and predetermined first and second luminance values.

As shown in FIG. 3(a), a fluorescence image G0 that the fluorescence-region identifying portion 33 receives from the fluorescence-image generating portion 32 includes a background region having weak luminance and a fluorescence region B having higher luminance than the luminance of the background region, that is, luminance due to fluorescence from the fluorescent dye. FIG. 3(b) is a graph showing the distribution of luminance values along A-A' in FIG. 3(a). The luminance value is nearly zero in a portion corresponding to the background region. In a portion corresponding to the fluorescence region B, the luminance value gradually increases from the background region, reaching a maximum luminance value at a center portion.

Figure 4:
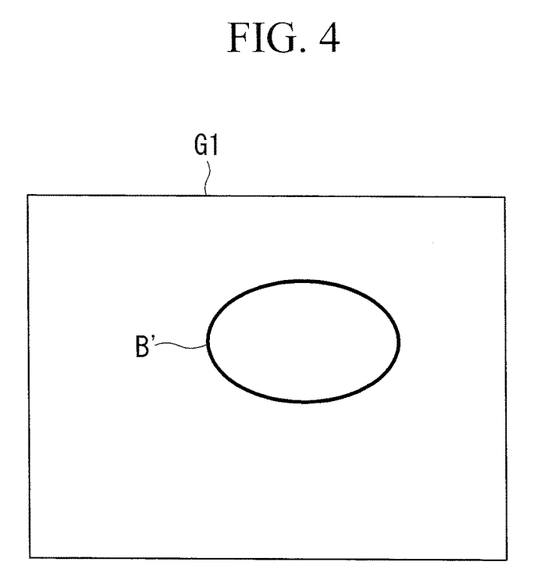
FIG. 4 is a diagram showing an identification image generated in a first image-processing mode by the fluorescence-region identifying portion in FIG. 2.

Specifically, in the first image-processing mode, the fluorescence-region identifying portion 33 identifies a region having a predetermined first luminance value (predetermined first fluorescence intensity) m, as shown in FIG. 3(b). Here, the predetermined first luminance value is determined to be a value that is sufficiently higher than the value of weak luminance exhibited by the background region and that is sufficiently lower than the luminance value due to the fluorescence from the fluorescent dye. In other words, the region identified in the first image-processing mode is an outline B' that surrounds substantially the entire fluorescence region B. As shown in FIG. 4, an identification image G1 generated in this way is an image in which substantially the entire fluorescence region B is shown as a region inside the outline B'. By doing so, in the subsequently generated superimposed image, a clear biological-tissue A image can also be displayed in the region from which the fluorescence is emitted while clearly displaying a boundary between the region from which fluorescence is emitted and the region from which fluorescence is not emitted.

In the second image-processing mode, the fluorescence-region identifying portion 33 identifies a region having a predetermined second luminance value n, which is higher than the predetermined first luminance value m, as shown in FIG. 3(b). In other words, the identified region having the predetermined second luminance value n is indicated by an outline of a region having a relatively high luminance value in the region surrounded by the outline B'. By doing so, the fluorescence region B can be identified through multiple steps based on the luminance value. The fluorescence-region identifying portion 33 generates an identification image G2 by displaying the region inside this outline by using a predetermined color.

Figure 5:
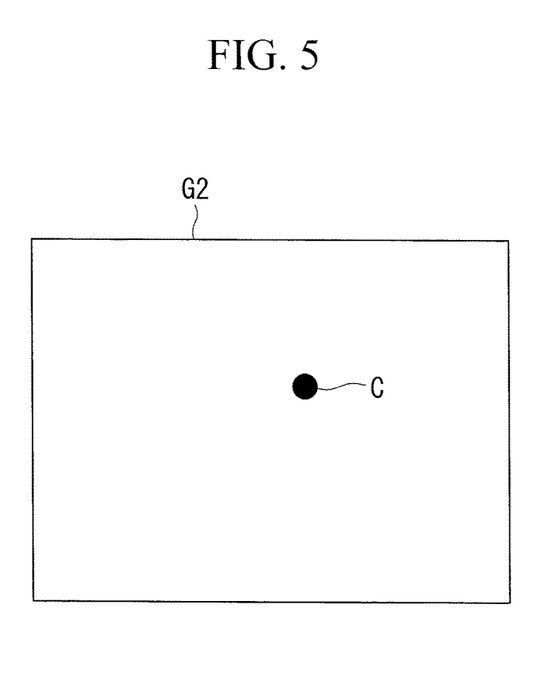
FIG. 5 is a diagram showing an identification image generated in a second image-processing mode by the fluorescence-region identifying portion in FIG. 2.

As shown in FIG. 5, the identification image G2 generated in this way is an image in which a relatively small marker C is added to the maximum-fluorescence region that includes a region where the fluorescence of the highest intensity in the fluorescence region B is detected, as well as regions in the vicinity of this region. Here, the luminance values of the individual pixels in the fluorescence image G0 are proportional to the density of biological molecules labeled with the fluorescent dye. In other words, the position at which the marker C is added indicates the region in which a disease is most advanced.

Note that, the method of identifying the maximum-fluorescence region and the entire fluorescence region B in the fluorescence image G0 is not limited to the method described above. For example, in the first image-processing mode, the fluorescence-region identifying portion 33 may select a pixel group having a luminance value equal to or greater than the predetermined first luminance value m. By doing so, under the first processing mode, the entire region in the biological tissue A from which the fluorescence is emitted, for example, the entire diseased region, can be presented to the operator. In addition, in the second image-processing mode, the fluorescence-region identifying portion 33 may select a pixel group having a luminance value equal to or greater than the predetermined second luminance value n. By doing so, under the second processing mode, a maximum-fluorescence region that includes the highest fluorescence intensity is identified, and thus, a region in the biological tissue A from which the most intense fluorescence is emitted, for example, a region in which a disease is most advanced, can be presented to the operator. The fluorescence-region identifying portion 33 may display the selected pixel groups in predetermined display modes, for example, by using predetermined colors.

The superimposed-image generating portion 34 generates a superimposed image by superimposing the identification image G1 or G2 generated by the fluorescence-region identifying portion 33 on the white-light image generated by the white-light-image generating portion 31. In other words, the superimposed image is an image in which, in a white-light image showing the shape of tissue in the body, substantially the entire fluorescence region B is specified by the outline B' or the maximum-fluorescence region is specified by the marker C. The superimposed-image generating portion 34 outputs the generated superimposed image to the output portion 36.

The image switching portion 35 possesses information in which types of the treatment tool 4 and the image-processing modes are associated with each other. Upon receiving the identification information (described later) from the IC tag reader 5, the image switching portion 35 selects an image-processing mode associated with the type of the treatment tool 4 (described later) included in the identification information and outputs a signal for setting the selected image-processing mode in the fluorescence-region identifying portion 33. For example, to the fluorescence-region identifying portion 33, the image switching portion 35 sets the first image-processing mode when the type of the treatment tool 4 is a scalpel and sets the second image-processing mode when the type of the treatment tool 4 is forceps.

Specifically, depending on which treatment tool 4 the operator selects to allow the IC tag reader 5 to read the IC tag 41 thereof, the image switching portion 35 switches between displaying the outline B' and displaying the marker C in the superimposed image generated by the superimposed-image generating portion 34.

In the initial state, the output portion 36 outputs the white-light image generated by the white-light-image generating portion 31 to the monitor 7. Then, upon receiving from the IC tag reader 5 the signal indicating that the IC tag 4 has been read, the output portion 36 switches the output to the monitor 7 to the superimposed image generated by the superimposed-image generating portion 34. The output portion 36 may be provided with a switch or the like that the operator operates to switch the image to be output between the white-light image and the superimposed image.

When the operator places the IC tag 41 attached to each treatment tool 4 over the IC tag reader 5, the IC tag reader 5 reads the identification information recorded in the IC tag 41. The identification information is recorded in the IC tag 41, including the type of the treatment tool 4 (treatment-details information) to which the tag is attached. Specifically, immediately before using a treatment tool 4, the operator allows the IC tag reader 5 to read the IC tag 41 of that treatment tool 4, and thus, the information about the details of the treatment to be applied to the observation subject is input to the IC tag reader 5. IC tag reader 5 transmits the read identification information to the image switching portion 35.

Next, the operation of the thus-configured fluorescence imaging apparatus 100 will be described.

To perform fluorescence imaging on the observation subject in the body by using the fluorescence imaging apparatus 100 according to this embodiment, by turning on the light source 21, the operator inserts the inserted portion 11 into the body while the white light and the excitation light are being radiated from the distal end of the inserted portion 11, and disposes the inserted portion 11 at a position where a diseased portion is displayed in the white-light image displayed on the monitor 7.

Next, the operator allows the IC tag reader 5 to read the IC tag 41 attached to the treatment tool 4 to be used in treating the diseased portion. By doing so, the display on the monitor 7 is switched from the white-light image to the superimposed image, and the outline B' or the marker C is displayed on the white-light image depending on the type of the treatment tool 4. Subsequently, the operator inserts this treatment tool 4 via the channel 12 of the endoscope 1 until reaching the diseased portion, and performs treatment on the region specified by the outline B' or the marker C in the superimposed image.

In this case, with this embodiment, the method of identifying the region to be specified in the superimposed image is switched in accordance with the details of the treatment to be performed by the operator. For example, when removing a diseased portion by using a scalpel, the entire region suspected of being diseased is specified by the outline B'; therefore, by removing the entire specified region, the diseased portion can be removed without allowing any of it to remain. On the other hand, when performing biopsy by using forceps, a region most suspected of being diseased is identified and specified by using the marker C; therefore, by collecting tissue from the specified position, an accurate examination result can be obtained in the biopsy.

In this way, it is possible to present to the operator, in the superimposed image, the optimal position to be treated in accordance with the details of the treatment. Therefore, there is an advantage in that the operator can perform appropriate treatment by simply treating the region specified by the outline B' or the marker C.

Note that, in this embodiment, the IC tag reader 5 that reads the IC tag 41 that identifies the treatment tool 4 has been described as an example of the treatment-information acquisition portion; alternatively, however, treatment-details information that indicates the details of the treatment may be acquired based on the treatment tool 4 displayed in the white-light image. The treatment-information acquisition portion is provided in the image processing unit 3.

For example, a treatment tool to which a label (not shown) indicating the type thereof is attached at the distal end may be used as the treatment tool 4; the treatment-information acquisition portion may detect the label in the white-light image; and the treatment-details information may be acquired in the form of the type of the treatment tool 4 indicated by the detected label. In addition, images of distal ends of treatment tools 4 may be stored in a storage portion (not shown) as reference images in association with the types of the treatment tools; the treatment-information acquisition portion may detect a treatment tool 4 in the white-light image by comparing the white-light image with the reference images; and the type of the detected treatment tool 4 may be acquired as the treatment-details information.

By doing so, the operator does not need to perform the operation for inputting the treatment-details information, and thus, the burden on the operator can be reduced.

In addition, in this embodiment, although the fluorescence-region identifying portion 33 identifies the fluorescence region by using the fluorescence intensity, alternatively, the fluorescence region may be identified by using a rate of change of the fluorescence intensity (luminance value).

Figure 6:
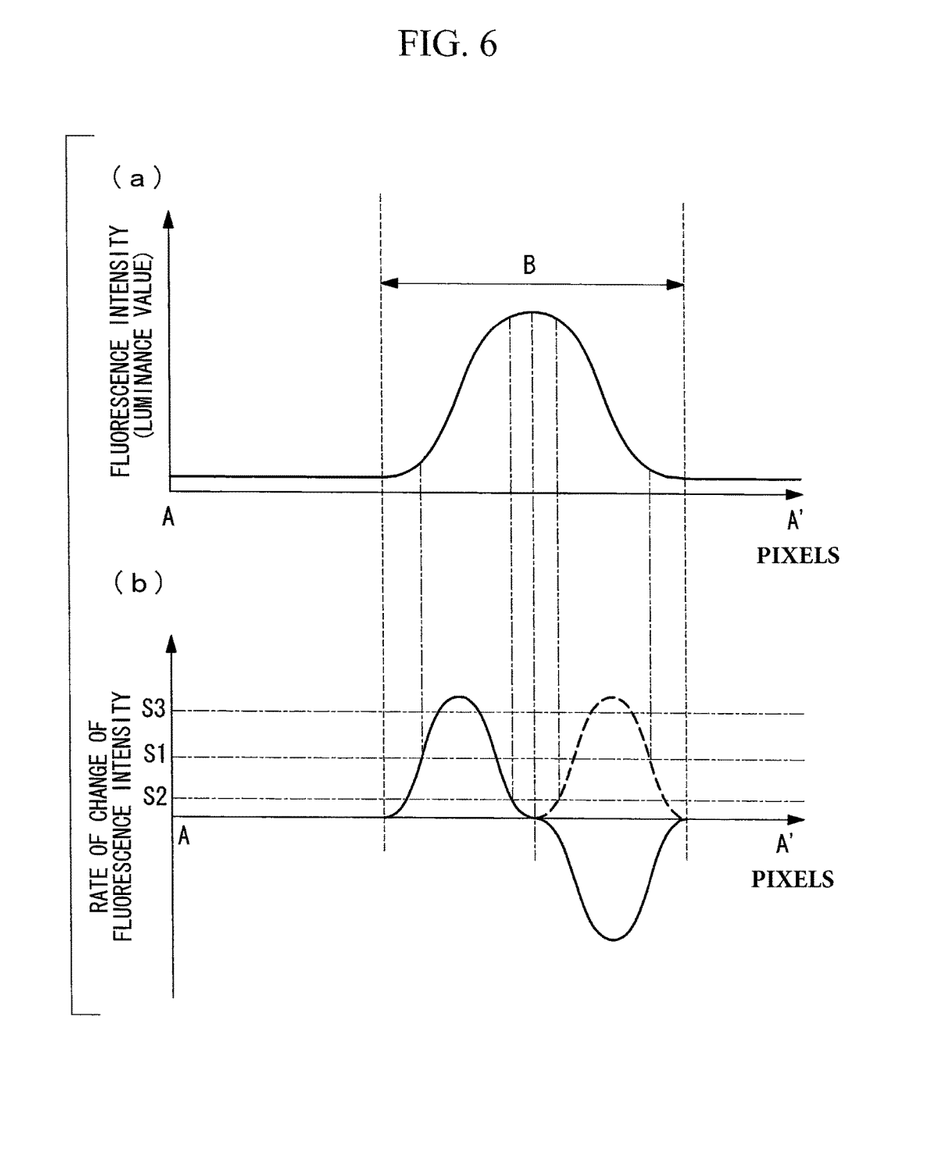
FIG. 6 is a diagram for explaining a modification of the imageprocessing performed by the fluorescence-region identifying portion in FIG. 2, in which (a) is a graph showing the fluorescence-intensity distribution in the fluorescence image, and (b) is a graph showing the rate of change in the fluorescence intensity in this fluorescence-intensity distribution.

FIG. 6(*a*) is a graph showing the distribution of the luminance values in the fluorescence image G0, and FIG. 6(*b*) is a graph showing the rate of change of the luminance values among adjacent pixels in the fluorescence image G0. In FIG. 6(*b*), the rate of change reaches a maximum at an intermediate position between the periphery of the fluorescence region B and the center thereof in the direction from A to A'; the rate of change reaches zero at the position where the fluorescence intensity reaches the maximum; and the rate of change reaches a maximum at an intermediate position in moving further toward the periphery.

The chain line in FIG. 6(*b*) indicates the absolute values of the rate of change. The fluorescence region is identified by using the absolute values of the rate of change of the luminance value. First, in the first image-processing mode, a region having a predetermined first rate of change S1, that is, the outline of the fluorescence region B, is identified. Although the fluorescence region B includes regions having the predetermined first rate of change S1 at two locations on each of the periphery side and the center side thereof, here, only the regions having lower luminance values are identified by using the information about the luminance values of the individual pixels shown in FIG. 6(*a*). By doing so also, as in the case of FIG. 3, it is possible to identify the outline B' of a relatively large region in which fluorescence is detected.

On the other hand, in the second image-processing mode, a region having a predetermined second rate of change S2 lower than the predetermined first rate of change S1 is identified. In this case also, the fluorescence region B includes regions having the predetermined second rate of change S2 at two locations on each of the periphery side and the center side thereof; however, only the regions inside the outline B' identified in the first processing mode are identified. In this way also, it is possible to identify a region having the highest luminance value in the region identified by using the first processing mode, and, similar to the case of FIG. 5, it is possible to generate the identification image G2 to which a marker C, which indicates the outline of a relatively small region in the region identified by using the first processing mode, is added.

Furthermore, as a third image-processing mode, a region having a predetermined third rate of change S3 may be identified.

In addition, in this embodiment, in the identification images G1 and G2, the entire fluorescence region is indicated by the outline B', and the maximum-fluorescence region is indicated by the marker C; however, these display modes are mere examples, and they can be appropriately changed.

Figure 7:
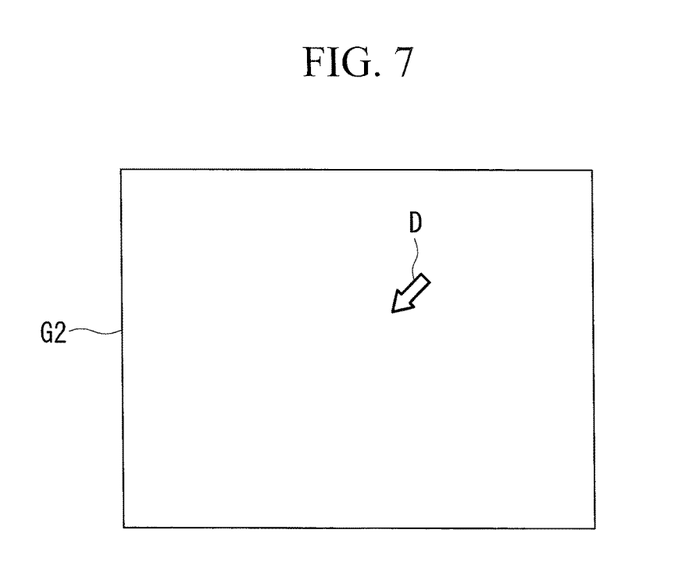
FIG. 7 is a diagram showing a modification of the identification image generated in the second image-processing mode by the fluorescence-region identifying portion.
Figure 8:
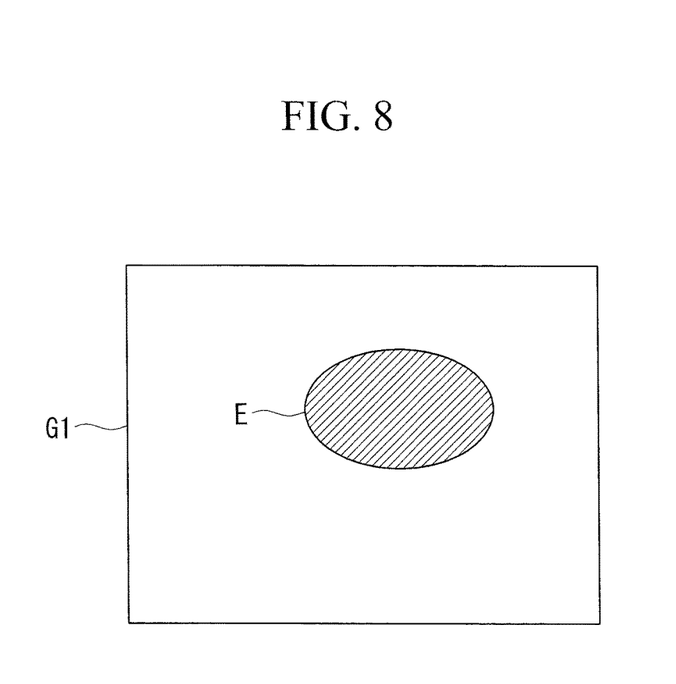
FIG. 8 is a diagram showing a modification of the identification image generated in the first image-processing mode by the fluorescence-region identifying portion.
Figure 9:
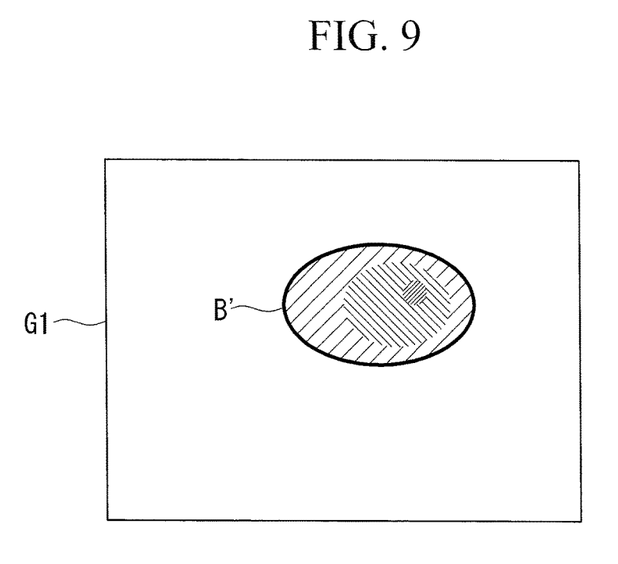
FIG. 9 is a diagram showing another modification of the identification image generated in the first image-processing mode by the fluorescence-region identifying portion.
Figure 10:
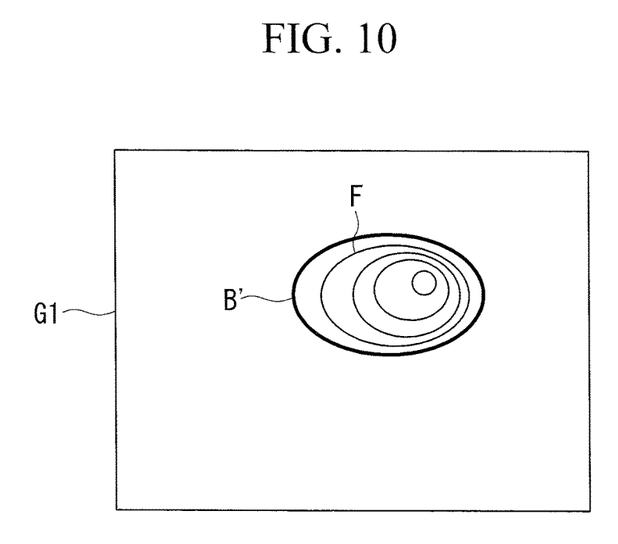
FIG. 10 is a diagram showing another modification of the identification image generated in the first image-processing mode by the fluorescence-region identifying portion.

As shown in FIG. 7, for example, in the second image-processing mode, an arrow D that indicates the identified maximum-fluorescence region may be displayed. As shown in FIG. 8, in the first image-processing mode, the entirety E of the identified fluorescence region may be displayed filled with a predetermined color. In this case, the region may be semi-transparently filled so that the tissue shape in the region of the white-light image overlapping with the filled region can be seen. In addition, as shown in FIG. 9, the area inside the outline B' may be filled with different colors depending on the luminance values so that the distribution the luminance values over the entire fluorescence region can be visualized or, as shown in FIG. 10, contour lines F that connect pixels having the same luminance values may be displayed.

In addition, in this embodiment, the image switching portion 35 switches the image-processing mode used by the fluorescence-region identifying portion 33 based on the identification information of the treatment tool 4; however, it suffices that the image switching portion 35 be configured so that the fluorescence region displayed in the superimposed image that is finally output to the monitor 7 can be switched between the maximum-fluorescence region and the entire fluorescence region in accordance with the details of the treatment.

For example, the image switching portion 35 may switch the superimposed image to be output from the output portion 36. Specifically, the fluorescence-region identifying portion 33 may always identify the fluorescence region in both the first image-processing mode and the second image-processing mode, and the superimposed-image generating portion 34 may generate two identification images G1 and G2 in which the maximum-fluorescence region and the entire fluorescence region are superimposed, respectively. Then, the image switching portion 35 may specify one of the superimposed images based on the acquired identification information of the treatment tool 4, and the specified superimposed image may be output to the monitor 7 from the output portion 36.

In addition, the image switching portion 35 may switch between the identification images G1 and G2 when superimposed on the white-light image at the superimposed-image generating portion 34. Specifically, the fluorescence-region identifying portion 33 may always generate the two identification images G1 and G2 in the first image-processing mode and the second image-processing mode; the image switching portion 35 may select one of the identification images G1 and G2 based on the acquired identification information of the treatment tool 4; and the image switching portion 35 may specify the selected identification image so as to be superimposed on the white-light image at the superimposed-image generating portion 34.

In addition, the method used by the fluorescence-region identifying portion 33 to identify the fluorescence region and the maximum-fluorescence region, described in this embodiment, is just an example, and it is not limited to this method. Also, the fluorescence-region identifying portion 33 may possess three or more image-processing modes.

For example, the fluorescence-region identifying portion 33 may generate a histogram of the luminance values in the fluorescence image G0 and may identify pixels whose frequencies correspond to predetermined proportions relative to the total frequencies in the generated histogram, where the pixels are identified in order starting from higher luminance values in the fluorescence image G0. At this time, three or more different values may be set in the fluorescence-region identifying portion 33 as the predetermined proportions relative to the total frequencies. For example, pixels corresponding to 5%, 10%, and 50% of the region in the fluorescence region may be identified in order starting from higher luminance values.

In addition, in this embodiment, an example in which the fluorescence imaging apparatus 100 is configured based on the endoscope 1 has been described; alternatively, however, the fluorescence imaging apparatus may be configured based on an optical microscope.

For example, when treating a body surface or the interior of a living organism by incising a body surface, this treatment is performed while observing a diseased portion from outside the living organism by using an optical microscope. In such a case also, a superimposed image can be generated by using a white-light image and a fluorescence image captured from outside the living organism by using the optical microscope, in a similar manner as in the embodiment described above; the method of identifying the fluorescence region to be superimposed in the superimposed image to be output to the monitor 7 can be switched in accordance with the details of the treatment; and thus, an optimal region to be treated can be presented to the operator in accordance with the details of the treatment.

REFERENCE SIGNS LIST 1 endoscope
2 illumination unit (illuminating portion)
4 treatment tool
5 IC tag reader (treatment-information acquisition portion)
13d imaging device (return-light imaging portion)
13e imaging device (fluorescence imaging portion)
33 fluorescence-region identifying portion
34 superimposed-image generating portion
35 image switching portion
36 output portion
100 fluorescence imaging apparatus
A biological tissue
B fluorescence region
G0 fluorescence image

The invention claimed is:
1. A fluorescence imaging apparatus comprising:
a light source configured to radiate excitation light and illumination light onto biological tissue;
a fluorescence imaging sensor configured to acquire a fluorescence image by imaging fluorescence emitted from the biological tissue due to irradiation by the excitation light;
a return-light imaging sensor configured to acquire a return-light image by imaging return light that returns from the biological tissue due to irradiation by the illumination light; and
a processor comprising hardware, wherein the processor is configured to:
acquire treatment-details information indicating specifics of a treatment to be performed on the biological tissue;
specify one or more processing condition to be used to process the fluorescence image from among a plurality of processing conditions in accordance with the treatment-details information;
in a case where a first processing condition is the one or more processing condition specified from among the plurality of processing conditions, identify a first fluorescence region in the fluorescence image having a predetermined first fluorescence intensity based on the first processing condition;
in a case where a second processing condition is the one or more processing condition specified from among the plurality of processing conditions, identify a second fluorescence region in the fluorescence image having a predetermined second fluorescence intensity based on the second processing condition; and
generate a superimposed image by superimposing the first fluorescence region or the second fluorescence region that is identified, with the return-light image at a region in the return-light image corresponding to the first fluorescence region or the second fluorescence region, respectively, that is identified.

2. The fluorescence imaging apparatus according to claim 1,
wherein in the case where the second processing condition is the processing condition specified from among the plurality of processing conditions, the processor is configured to identify a maximum-fluorescence region that includes the highest fluorescence intensity inside the second fluorescence region.

3. The fluorescence imaging apparatus according to claim 2,
wherein the processor is configured to generate the superimposed image by superimposing an outline of the first fluorescence region on the return-light image.

4. The fluorescence imaging apparatus according to claim 1,
wherein the processor is configured to generate the superimposed image by superimposing an outline of the first fluorescence region on the return-light image.

5. The fluorescence imaging apparatus according to claim 1,
wherein the processor is configured to receive an identification information inputted by an operator, wherein the identification information identifies a treatment tool as the treatment-details information.

6. The fluorescence imaging apparatus according to claim 1,
wherein the processor is configured to:
detect a treatment tool in the return-light image; and
identify a type of the detected treatment tool as the treatment-details information.

7. A fluorescence imaging apparatus comprising:
a light source configured to radiate excitation light and illumination light onto biological tissue;
a fluorescence imaging sensor configured to acquire a fluorescence image by imaging fluorescence emitted from the biological tissue due to irradiation by the excitation light;
a return-light imaging sensor configured to acquire a return-light image by imaging return light that returns from the biological tissue due to irradiation by the illumination light; and
a processor comprising hardware, wherein the processor is configured to:
acquire treatment-details information indicating specifics of a treatment to be performed on the biological tissue;
specify one or more processing conditions to be used to process the fluorescence image from among a plurality of processing conditions in accordance with the treatment-details information;

in a case where a first processing condition is the one or more processing conditions specified from among the plurality of processing conditions, identify a first fluorescence region in the fluorescence image having fluorescence intensities equal to or greater than a predetermined first fluorescence intensity based on the first processing condition;

in a case where a second processing condition is the one or more processing conditions specified from among the plurality of processing conditions, identify a second fluorescence region in the fluorescence image having fluorescence intensities equal to or greater than a predetermined second fluorescence intensity that is greater than the predetermined first fluorescence intensity based on the second processing condition; and generate a superimposed image by superimposing the first fluorescence region and/or the second fluorescence region that is identified, with the return-light image at a region in the return-light image corresponding to the first fluorescence region and/or the second fluorescence region, respectively, that is identified.

8. The fluorescence imaging apparatus according to claim 7, wherein in the case where the second processing condition is the processing condition specified from among the plurality of processing conditions, the processor is configured to identify a maximum-fluorescence region that includes the highest fluorescence intensity inside the second fluorescence region.

9. The fluorescence imaging apparatus according to claim 8, wherein the processor is configured to generate the superimposed image by superimposing an outline of the first fluoresce region on the return-light image.

10. The fluorescence imaging apparatus according to claim 7, wherein the processor is configured to generate the superimposed image by superimposing an outline of the first fluorescence region on the return-light image.

11. A fluorescence imaging apparatus comprising:

a light source configured to radiate excitation light and illumination light onto biological tissue;

a fluorescence imaging sensor configured to acquire a fluorescence image by imaging fluorescence emitted from the biological tissue due to irradiation by the excitation light;

a return-light imaging sensor configured to acquire a return-light image by imaging return light that returns from the biological tissue due to irradiation by the illumination light; and a processor comprising hardware, wherein the processor is configured to:

acquire treatment-details information indicating specifics of a treatment to be performed on the biological tissue;

specify one or more processing conditions to be used to process the fluorescence image from among a plurality of processing conditions in accordance with the treatment-details information;

in a case where a first processing condition is the one or more processing conditions specified from among the plurality of processing conditions, identify a first fluorescence region in the fluorescence image in which luminance values thereof change at a predetermined first rate of change based on the first processing condition;

in a case where a second processing condition is the one or more processing conditions specified from among the plurality of processing conditions, identify, inside the first fluorescence region, a second fluorescence region in the fluorescence image in which luminance values thereof change at a predetermined second rate of change based on the second processing condition; and generate a superimposed image by superimposing the first fluorescence region or the second fluorescence region that is identified, with the return-light image at a region in the return-light image corresponding to the first fluorescence region or the second fluorescence region, respectively, that is identified.

12. The fluorescence imaging apparatus according to claim 11, wherein the predetermined second rate of change is lower than the predetermined first rate of change.

* * * * *